United States Patent [19]

Pech et al.

[11] Patent Number: 5,523,425
[45] Date of Patent: Jun. 4, 1996

[54] PROCESS FOR PRODUCING CHLOROHYDRINS

[75] Inventors: Gunther A. Pech, Winsen; Werner J. Witzl, Königsmarckstr, both of Germany

[73] Assignee: The Dow Chemical Company, Midland, Mich.

[21] Appl. No.: 361,067

[22] Filed: Dec. 21, 1994

[51] Int. Cl.⁶ .................. C07D 301/26; C07D 303/08; C07C 29/66; C07C 31/36

[52] U.S. Cl. .................. 549/522; 568/847; 568/850; 549/521

[58] Field of Search .................. 568/850, 847; 549/522, 521

[56] References Cited

U.S. PATENT DOCUMENTS

| | | | |
|---|---|---|---|
| 1,295,339 | 2/1919 | McElroy | 568/850 |
| 1,589,359 | 6/1926 | Burdick | 549/522 |

FOREIGN PATENT DOCUMENTS

| | | | |
|---|---|---|---|
| 0016433 | 10/1980 | European Pat. Off. | |
| 553376 | 8/1993 | European Pat. Off. | 568/850 |
| 1557589 | 2/1969 | France . | |
| 0144907 | 11/1980 | Germany . | |
| 3145481 | 6/1991 | Japan . | |

OTHER PUBLICATIONS

Billet, Reinhard, "Industrielle Destillation", *Verlag Chemie*, Weinheim, (1973), pp. 89–103, 259–262, 301–305 and 455–464.

*Primary Examiner*—Joseph E. Evans

[57] ABSTRACT

In a process for producing a chlorohydrin an olefinically unsaturated compound is reacted with chlorine in the presence of water. Water is applied as a film on a solid support in a reaction zone and/or water droplets are dispersed in the reaction zone. The reaction is conducted at a pressure of up to about 10 bar.

20 Claims, No Drawings

PROCESS FOR PRODUCING CHLOROHYDRINS

BACKGROUND OF THE INVENTION

The present invention relates to a process for producing a chlorohydrin by reacting an olefinically unsaturated compound with chlorine in the presence of water.

East German Patent 144,907 discloses a process for the continuous production of aqueous propylene chlorohydrin by reacting propylene and chlorine in the presence of water in a bubble column. The bubble column is completely filled with the reaction mixture. The gas volume should be minimized or gas avoided in the bubble column. The reaction products are removed from the column via a conical head section. They are separated into an aqueous phase and a gaseous phase only outside the bubble column. Unfortunately, a temperature and pressure gradient is observed over the reactor, i.e., the temperature and pressure are not constant over the entire length of the column. Furthermore, the process water demand in the reaction is very high. Moreover, the organic products do not readily evaporate but an organic liquid phase may be formed which increases the tendency to the formation of by-products.

Published European Patent Application 0,016,433 discloses that in known processes for producing chlorohydrins chlorine and propylene are reacted continuously in a large excess of water at ambient or slightly elevated pressure. A portion of the solution of propylene chlorohydrin containing hydrochloric acid which is produced is recycled to the reactor because chlorine is said to be much more soluble in aqueous hydrochloric acid than in water. European Patent Application 0,0.16,433 suggests a continuous production of propylene chlorohydrin by reacting chlorine and propylene in an aqueous solution at 20° C. to 80° C. wherein chlorine, propylene and water are reacted in a co-current stream at a pressure between 15 and 40 bar without recycling a portion of the reaction product mixture. Propylene and chlorine are used in a molar ratio of (1.0 to 2.0):1. The amount of water is 10 to 50 liters per kg of chlorine. The starting materials are fed in gaseous or liquid form in a fine distribution into a tubular reactor. The European Patent application recommends avoiding a gas phase in the reactor in order to reduce the amount of by-products that are formed in the reaction. Unfortunately, the organic products do not readily evaporate but an organic liquid phase may be formed which increases the tendency for the formation of by-products.

French Patent 1,557,589 discloses a process for producing dichlorohydrins by dispersing allyl chloride in a large amount of water and then contacting it with chlorine. It is suggested to conduct the reaction in a reactor with rotating pallets. Unfortunately, the process water demand is very high in the suggested process. The organic products are practically insoluble in water and form an organic phase in which secondary reactions take place. This organic phase has to be separated rapidly from the aqueous solution which contains the dichlorohydrins. However, secondary reactions wherein by-products are formed are highly undesirable.

DERWENT abstract AN 91-226460, abstracting JP-A-3,145,481 suggests the preparation of epichlorohydrins by reacting 2,3-dichloro-1-propanol and/or 1,3-dichloro-2-propanol with an alkaline solution. However, this reaction makes use of other starting materials.

In view of the deficiencies of the processes disclosed in the prior art, it is desirable to provide an improved process for producing chlorohydrins.

SUMMARY OF THE INVENTION

One aspect of the present invention is a process for producing a chlorohydrin by reacting an olefinically unsaturated compound with chlorine in the presence of water in a reaction zone wherein water is a) applied as a film on a solid support, or b) dispersed as droplets, or c) applied as a film on a solid support and dispersed as droplets in the reaction zone and the reaction is conducted at a pressure of up to about 10 bar.

Another aspect of the present invention is a process for producing an oxide, which process comprises producing a chlorohydrin by the above-mentioned process and converting the produced chlorohydrin to the corresponding oxide.

DETAILED DESCRIPTION OF THE INVENTION

Olefinically unsaturated compounds which are useful as starting materials in the process of the present invention are linear or branched, optionally halogenated hydrocarbons containing 2 to 5 carbon atoms, such as ethylene, propylene, isobutylene, butene-1, cisor trans-butene-2, 1,3-butadiene, chlorinated olefinically unsaturated hydrocarbons such as allyl chloride ( 3-chloro-1-propene).

Most preferably propylene, allyl chloride or butylene are used as starting materials for producing propylene oxide, epichlorohydrin or butylene oxide. The olefinically unsaturated compound and the chlorine can both be fed as liquids or both as gases to the reaction zone; or one of these components can be fed as a gas and the other one as a liquid to the reaction zone. The olefinically unsaturated compound and the chlorine can be fed separately as counter-current or, preferably, as co-current streams into the reaction zone. Most preferably the olefinically unsaturated compound and the chlorine are fed as a single stream or as separate streams co-currently to the direction in which water is fed to the reaction zone. The olefinically unsaturated compound and chlorine preferably have a temperature of about −30° C. to about 200° C., more preferably of about 20° C. to about 140° C., most preferably of about 60° C. to about 110° C. when they are fed into the reaction zone. Although the olefinically unsaturated compound and chlorine can be premixed, preferably they are fed into the reaction zone as separate streams, more preferably as separate gas streams. Advantageously, the olefinically unsaturated compound and the chlorine are fed at the top into the reaction zone. Most preferably, a continuous gas phase is maintained in the reaction zone wherein liquid water is dispersed. The molar ratio between the olefinically unsaturated compound and chlorine generally is from about (0.5 to 2):1, preferably from about (0.7 to 1.3):1, more preferably from about (0.9 to 1.1):1.

Liquid water is applied as film on a solid support in the reaction zone and/or water droplets are dispersed in the reaction zone. The water can be applied as a film in the reaction zone with the aid of known devices, such as box-type distributors, sieve tray distributors, concentric or straight pipe distributors. The film generally has a thickness of about 0.05 to about 10 mm, preferably of about 0.1 to about 5 mm, more preferably of about 0.5 to about 3 mm. The solid support in the reaction zone can be one or more reactor walls or things comprised or built in the reactor, such as distillation trays or a random or structured packing.

Useful distillation trays are bubble trays, tunnel trays, sieve trays, centrifugal trays or valve trays. Useful random packings are pall rings or interpack fillings. Preferably, a structured packing is used, such as a grid packing, a square-grid packing or, more preferably, a fabric packing. Most preferably, a fabric packing of high specific surface area is used. Structured packings are preferred over the distillation trays or random packings. Distillation trays and packings are generally described by R. Billet, *Industrielle Destillation* (Industrial Distillation), Verlag Chemie, Weinheim, 1973, pp. 94–103 and pp. 301–305.

Known water distributors can be used for dispersing water droplets in the reaction zone. Useful water distributors are, for example, distributors equipped with spray nozzles or atomizers. Such liquid distributors are generally described by R. Billet, *Industrielle Destillation* (Industrial Distillation), Verlag Chemie, Weinheim, 1973, pp. 455–458. Water spray nozzles are preferred in the practice of the present invention. The dispersed droplets generally have a diameter of up to about 5 mm, preferably of from about 1 to about 1,000 micrometers, more preferably from about 10 to about 500 micrometers. The water generally has a temperature of about 0° C. to about 200° C., preferably of about 50° C. to about 150° C., more preferably of about 80° C. to about 120° C. when it is fed into the reaction zone. Most preferably, it is fed into the reaction zone at the boiling temperature of the product mixture at the prevailing pressure in the reaction zone.

Preferably, a combination of one or more spray nozzles and a structured packing is used in the process of the present invention. Most preferably, liquid water is fed into the reaction zone by means of at least one spray nozzle which is mounted at the top of the reaction zone. An optimal distribution of liquid water in the gaseous chlorine and olefinically unsaturated compound is thereby achieved. The weight ratio between water and the olefinically unsaturated compound generally is about (3 to 100):1, preferably about (20 to 70):1, more preferably about (25 to 35):1. As compared with the process taught in East German Patent 144,907, the process water demand in the process of the present invention is significantly reduced.

In addition to the olefinically unsaturated compound, chlorine and liquid water, optional compounds can be fed into the reaction zone. For example, steam or an inert gas, such as nitrogen can be fed into the reaction zone in order to increase the efficiency of removing the products and by-products of the reaction and/or in order to reduce the formation of by-products. If steam or an inert gas is utilized, the weight ratio between steam or the inert gas and the olefinically unsaturated compound generally is about (0.1 to 10):1, more preferably about (0.5 to 5):1, most preferably about (0.7 to 1.3):1. Furthermore, the water which is fed into the reaction zone can contain one or more optional compounds, such as an alkali chloride like sodium chloride or calcium chloride, or hydrogen chloride. A part of the aqueous phase which is produced in the process of the present invention can be recycled to the reaction zone as aqueous hydrochloric acid. If present, the concentration of such additives generally is from about 0.1 to about 5 mols, preferably from about 0.5 to about 3 mols, more preferably from about 1.0 to about 2.0 mols per liter of aqueous solution.

In the process of the present invention the liquid water phase is dispersed in a gas phase, preferably in a continuous gas phase. The gaseous olefinically unsaturated compound and chlorine are absorbed on the liquid water surface and reacted. In contrast to the process taught in East German Patent 144,907, the volume of the liquid in the reaction zone is smaller than the gas volume in the reaction zone. The reaction is preferably conducted continuously. The process of the present invention can be conducted in one reactor or in several reactors which are arranged one after the other. Preferably one or more tubular reactors are used, most preferably one or more spray towers. The reaction temperature preferably is from about 0° to about 200 ° C., more preferably from about 50° C. to about 150° C., most preferably from about 80° C. to about 120° C. The reaction can be conducted under isothermal or adiabatic conditions. Isothermal conditions are preferred. The heat of reaction can be removed by evaporating a portion of the reaction mixture. Preferably, at least a portion of the water and the major portion of the produced chlorohydrin and by-products evaporate during the reaction. When most of the produced chlorohydrin and by-products evaporate, the formation of an organic liquid phase is avoided. The lack of an organic liquid phase is highly preferred because the components of such an organic liquid phase would tend to react with chlorine in the absence of water and form undesirable by-products. Under adiabatic conditions the pressure is up to about 10 bar, preferably from about 0.1 to about 5 bar, more preferably from about 0.5 to about 5 bar, most preferably from about 0.7 to about 3.0 bar. Under isothermal conditions the pressure is up to about 10 bar, preferably from about 0.1 to about 5 bar, more preferably from about 0.5 to about 2.0 bar, most preferably from about 0.7 to about 1.3 bar. Most preferably, the reaction is conducted isothermally at about atmospheric pressure and a temperature of about 100° C.

The produced reaction mixture is preferably divided into a gaseous outlet stream and a liquid outlet stream and the gaseous and liquid outlet streams are removed from the reaction zone.

The gaseous outlet stream generally contains the main portion of the produced chlorohydrin as well as volatile by-products, such as excess chlorine, excess amounts of the olefinically unsaturated compound, dichlorohydrins, aliphatic dichloro compounds, dichloroethers and other by-products, depending on the olefinically unsaturated compound which has been used as a starting material. When propylene has been used as a starting material, other by-products are, for example, dichloropropane, trichloropropane, dichloropropanols or dichloroisopropylether.

The liquid outlet stream is an aqueous phase and mainly contains hydrogen chloride dissolved in water. The aqueous liquid phase generally contains minor amounts of organic by-products, such as those mentioned above. Generally, the weight of the organic by-products is from about 0.01 to about 0.5 percent, typically from about 0.1 to about 0.4 percent, based on the total weight of the aqueous liquid phase. A portion or the entire amount of the liquid outlet stream can be recycled back to the reaction zone as liquid feed.

The liquid and gaseous outlet streams are optionally further purified in a known manner.

According to the preferred embodiments of the present invention the yield of the produced chlorohydrin generally is at least about 80 percent, typically at least about 85 percent, in many cases even about 90 percent or more, depending on the amount of water used in the reaction.

The produced chlorohydrin can be reacted to the corresponding oxide in a known manner. For example, propylene chlorohydrin can be reacted to propylene oxide. The reaction can be conducted in a known manner by subjecting the chlorohydrin to a dehydrochlorination with the aid of a strong base, such as an alkali metal or alkaline earth metal hydroxide. Such a dehydrochlorination process is known in the art and, for example, described in published German Patent Applications DT-1,291,328 and DE-A-1,643,847 or French Patent Application 1,594,349.

The process of the present invention is further illustrated by the following examples which should not be construed to limit the scope of the invention. Unless otherwise indicated, all parts and percentages are by weight.

EXAMPLE 1

69 parts/hour of propylene gas and 116 parts/hour of chlorine gas at a temperature of 20° C. are contacted with 2685 parts/hour of water at a temperature of 100° C. in a co-currently operated reactor at atmospheric pressure. No steam or inert gas is additionally fed into the reactor. The propylene gas and chlorine are fed at the top into the column. Water is distributed in the column by means of a spray nozzle mounted at the top of the column. The dispersed water droplets have an average diameter of about 400 micrometers. A fabric packing of the type BX, commercially available from Sulzer, Switzerland, is built into the column.

During the reaction a bottoms temperature of 98° C. is observed. 193 parts/hour of vapor phase are withdrawn from the column. A yield of propylene chlorohydrin of 92.9 percent is achieved. The liquid outlet stream which is withdrawn from the reactor mainly consists of aqueous hydrochloric acid. The major organic by-product in the liquid outlet stream is 1,2-dichloropropane. Its concentration is only 0.03 percent, based on the total weight of the liquid stream. Accordingly, no separate organic liquid phase is observed in the liquid outlet stream.

EXAMPLE 2

188 parts/hour of propylene gas and 316 parts/hour of chlorine gas at a temperature of 20° C. are contacted with 2632 parts/hour of water at a temperature of 100° C. in a co-currently operated reactor at atmospheric pressure. No steam or inert gas is additionally fed into the reactor. The same type of reactor, spray nozzle and packing is used as in Example 1.

During the reaction a bottoms temperature of 98.5° C. is observed. 637 parts/hour of vapor phase are withdrawn from the column. A yield of propylene chlorohydrin of 86.0 percent is achieved. The liquid outlet stream which is withdrawn from the reactor mainly consists of aqueous hydrochloric acid. The major organic by-product in the liquid outlet stream is 1,2-dichloropropane. Its concentration is only 0.13 percent, based on the total weight of the liquid stream. Accordingly, no separate organic liquid phase is observed in the liquid outlet stream.

EXAMPLE 3

76 parts/hour of propylene gas and 128 parts/hour of chlorine gas at a temperature of 20° C. are contacted with 2538 parts/hour of an aqueous solution of sodium chloride at a temperature of 100° C. in a co-currently operated reactor at atmospheric pressure. The concentration of sodium chloride is 1 mole/liter. No steam or inert gas is additionally fed into the reactor. The same type of reactor, spray nozzle and packing is used as in Example 1.

During the reaction a bottoms temperature of 97.5° C. is observed. 198 parts/hour of vapor phase is withdrawn from the column. A yield of propylene chlorohydrin of 84.5 percent is achieved. The liquid outlet stream which is withdrawn from the reactor mainly consists of aqueous hydrochloric acid. The major organic by-product in the liquid outlet stream is 1,2-dichloropropane. Its concentration is only 0.13 percent, based on the total weight of the liquid stream. Accordingly, no separate organic liquid phase is observed in the liquid outlet stream.

What is claimed is:

1. A process for producing a chlorohydrin which comprises reacting an olefinically unsaturated compound with chlorine in the presence of water in a reaction zone; wherein the water is a) applied as a film on a solid support, or
   b) dispersed as droplets, or
   c) applied as a film on a solid support and dispersed as droplets in the reaction zone, the reaction is conducted at a pressure of up to about 10 bar, and the weight ratio between water and the olefinically unsaturated compound is from about 3:1 to about 100:1.

2. The process of claim 1 wherein the olefinically unsaturated compound, chlorine and water are fed co-currently into the reaction zone.

3. The process of claim 1 wherein the weight ratio between water and the olefinically unsaturated compound is from about 20:1 to about 70:1.

4. The process of claim 1 wherein the reaction is conducted at a pressure of from about 0.1 to about 5 bar.

5. The process of claim 1 wherein the reaction is conducted at a temperature of from 50° C. to 150° C.

6. The process of claim 1 wherein distillation trays or a random or structured packing are/is comprised in the reaction zone.

7. The process of claim 3 wherein distillation trays or a random or structured packing are/is comprised in the reaction zone.

8. The process of claim 4 wherein distillation trays or a random or structured packing are/is comprised in the reaction zone, 9. The process of claim 1 wherein at least a portion of the water and the major portion of the produced chlorohydrin and by-products evaporate during the reaction.

10. The process of claim 3 wherein at least a portion of the water and the major portion of the produced chlorohydrin and by-products evaporate during the reaction.

11. The process of claim 4 wherein at least a portion of the water and the major portion of the produced chlorohydrin and by-products evaporate during the reaction.

12. The process of claim 1 wherein the produced reaction mixture is divided into a gaseous stream and a liquid stream.

13. The process of claim 12 wherein at least a portion of the liquid stream is recycled to the reaction zone.

14. The process of claim 1 wherein propylene, allyl chloride or butylene is reacted with chlorine.

15. The process of claim 3 wherein propylene, allyl chloride or butylene is reacted with chlorine.

16. The process of claim 4 wherein propylene, allyl chloride or butylene is reacted with chlorine.

17. A process for producing an oxide, which process comprises the steps of

I) producing a chlorohydrin by reacting an olefinically unsaturated compound with chlorine in the presence of water in a reaction zone, wherein the water is a) applied as a film on a solid support, or
   b) dispersed as droplets, or
   c) applied as a film on a solid support and dispersed as droplets in the reaction zone, the reaction is conducted at a pressure of up to about 10 bar, and the weight ratio between water and the olefinically unsaturated compound is from about 3:1 to about 100:1 and II) converting the produced chlorohydrin to the corresponding oxide.

18. The process of claim 17, wherein the reaction in step I) is conducted at a pressure of from about 0.1 to about 5 bar.

19. The process of claim 17, wherein propylene, allyl chloride or butylene is reacted with chlorine in step I).

20. The process of claim 1 wherein the olefinically unsaturated compound is a linear or branched hydrocarbon or halogenated hydrocarbon containing from 2 to 5 carbon atoms.

* * * * *